(12) United States Patent
Insana et al.

(10) Patent No.: US 8,398,550 B2
(45) Date of Patent: Mar. 19, 2013

(54) TECHNIQUES TO EVALUATE MECHANICAL PROPERTIES OF A BIOLOGIC MATERIAL

(75) Inventors: Michael F. Insana, Urbana, IL (US);
Marko Orescanin, Urbana, IL (US);
Kathleen Toohey, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 506 days.

(21) Appl. No.: 12/592,717

(22) Filed: Dec. 1, 2009

(65) Prior Publication Data

US 2010/0191110 A1    Jul. 29, 2010

Related U.S. Application Data

(60) Provisional application No. 61/200,543, filed on Dec. 1, 2008.

(51) Int. Cl.
*A61B 8/00* (2006.01)
(52) U.S. Cl. ........................................ 600/438
(58) Field of Classification Search ........... 600/438
See application file for complete search history.

(56) References Cited

U.S. PATENT DOCUMENTS

| | | | |
|---|---|---|---|
| 4,982,339 A | 1/1991 | Insana et al. | |
| 5,810,731 A | 9/1998 | Sarvazyan et al. | |
| 6,277,074 B1 | 8/2001 | Chaturvedi et al. | |
| 7,022,077 B2 | 4/2006 | Mourad et al. | |
| 7,252,004 B2 | 8/2007 | Fink et al. | |
| 7,444,875 B1 | 11/2008 | Wu et al. | |
| 2005/0054930 A1 | 3/2005 | Rickets et al. | |
| 2005/0165306 A1 | 7/2005 | Zheng et al. | |
| 2005/0203398 A1 | 9/2005 | Sandrin et al. | |
| 2005/0215899 A1 | 9/2005 | Trahey et al. | |
| 2007/0038095 A1 | 2/2007 | Greenleaf et al. | |
| 2008/0200805 A1 | 8/2008 | Hoyt et al. | |
| 2008/0255444 A1 | 10/2008 | Li | |
| 2009/0005682 A1 | 1/2009 | Fan et al. | |
| 2009/0116032 A1 | 5/2009 | Zara | |
| 2009/0163805 A1 | 6/2009 | Sunagawa et al. | |
| 2009/0216119 A1 | 8/2009 | Fan et al. | |
| 2009/0216131 A1 | 8/2009 | Chase et al. | |

FOREIGN PATENT DOCUMENTS

WO    WO 2007/110375 A1    10/2007

OTHER PUBLICATIONS

Orescanin, et al., Material Properties from Acoustic Radiation Force Step Response, Material Property Estimation, Sep. 22, 2008.

*Primary Examiner* — Brian Casler
*Assistant Examiner* — Saurel J Selkin
(74) *Attorney, Agent, or Firm* — Krieg DeVault LLP

(57) ABSTRACT

A system includes an acoustic radiation force source that is structured to generate an acoustic radiation force at one or more frequencies. A shear wave transmission device is embedded in a mass including a biologic material. The shear wave transmission device is responsive to the acoustic radiation force source to transmit shear waves through the biologic material. A Doppler ultrasonic device detects the shear waves and generates data representative of the shear waves. A processing device determines one or more mechanical properties of the biologic material from the data.

24 Claims, 11 Drawing Sheets

TECHNIQUES TO EVALUATE MECHANICAL PROPERTIES OF A BIOLOGIC MATERIAL

CROSS REFERENCE TO RELATED APPLICATIONS

The present application claims the benefit of U.S. Provisional Patent Application No. 61/200,543, filed Dec. 1, 2008, which is hereby incorporated by reference in its entirety.

GOVERNMENT RIGHTS

The present invention was made with Government assistance from the National Cancer Institute under award number ROI CA082497. The Government has certain rights in this invention.

BACKGROUND

The present application relates to evaluation of biologic materials, and more particularly, but not exclusively, relates to the evaluation of biologic materials with shear waves.

Elasticity imaging is a promising diagnostic technique for discriminating between benign and malignant tumors, such as breast lesions. Generally, such diagnostic value stems from the role of the cellular mechano-environment in regulating tumor growth, and from the tumor contrast observed for various mechanical properties, such as elasticity. Unfortunately, the visibility of lesions in elasticity imaging can vary widely. Thus, there is a need for further contributions in this area of technology.

SUMMARY

One embodiment of the present application provides a unique technique for evaluating biologic material. Other embodiments include unique methods, systems, devices, and apparatus to evaluate one or more mechanical characteristics of biologic materials, or the like. Further embodiments, forms, features, aspects, benefits, and advantages of the present application shall become apparent from the description and figures provided herewith.

DETAILED DESCRIPTION OF REPRESENTATIVE EMBODIMENTS

Figure 1:
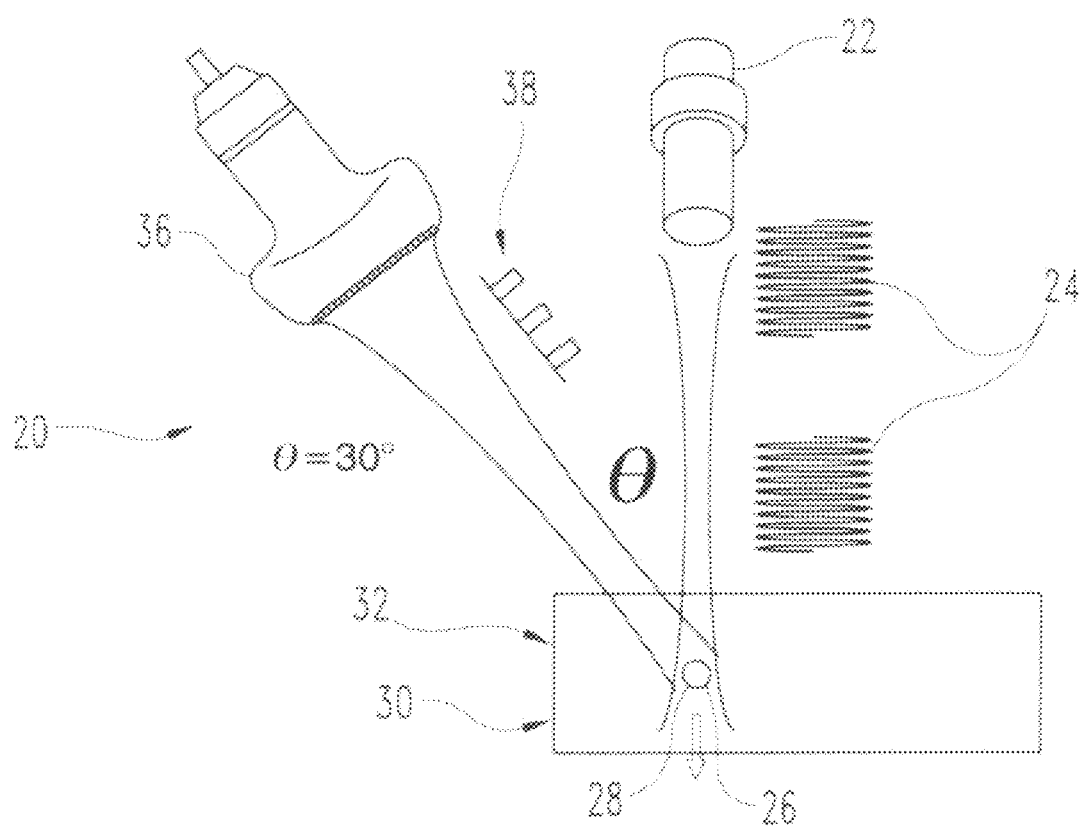
FIG. 1 is a diagrammatic view of a system to measure viscoelastic properties of a sample including a gel. Acoustic force applied by a source transducer displaces a sphere embedded in the gel. An imaging transducer tracks the induced motion of the sphere.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One aspect of the present application explores the use of 3-D cell cultures to evaluate relationships between the physical and biological sources of contrast across the spectrum of acoustic radiation force frequencies used in elasticity imaging. This type of culture may include living cells, such as mammary cells, embedded in a hydrogel volume. These cells can be biochemically or mechanically stimulated and then observed under sterile conditions. Such cultures can mimic the responses of tumor-cell clusters to their microenvironment. Further, gels combine geometric simplicity for ease of mechanical measurements with dynamic cellular processes that can be independently verified via optical microscopy.

Many biological tissues and various gels considered are biphasic polymers, which means their mechanical properties are determined by a polymeric matrix (solid phase) embedded in a liquid (fluid phase). The mechanical responses of multiphasic polymers depend significantly on the rate at which force is applied. For example, the complex shear modulus is known to vary widely with force frequency in lightly-cross-linked amorphous polymers, breast tissues, and even within individual cells of the body.

A radiation force technique can be used to estimate shear modulus and shear viscosity of gel types often used in 3-D cell cultures and engineered tissues. Particle velocity estimates can be determined from modulus and viscosity through a second-order rheological model, and the results provide an estimate of the impulse response function of shear wave imaging.

Non-limiting benefits of certain embodiments include: (1) provision of a tool that enables investigators to discover the role of the mechano-environment in cell propagation and disease progression, (2) use of such discoveries to refine elasticity imaging and discrimination between different tumor types and/or between lesions and healthy tissue, (3) measurement of mechanical changes in engineered tissues as cell grow, in vitro or in vivo, and (4) when the medium is vibrated with a biopsy needle, tissue samples may later be extracted for pathology or examined.

To better evaluate and model cell cultures, tissues, and other biologic material applications, gel-based media have been characterized through simulation and empirically. In one system, a strongly scattering sphere is embedded in the gel. Scattering from the sphere efficiently couples the acoustic field to the gel to induce forces that measurably deform gels and the cells at relatively low acoustic intensity. For sphere diameters that are small compared with the beamwidth (1.5 mm and 6 mm, respectively), local plane waves can be assumed and the time-averaged force on the scattering sphere is approximately given by equation (1) as follows:

$$F = \pi \alpha^2 Y \bar{E}. \tag{1}$$

The quantity α is the sphere radius and Y is the radiation force function as determined by the mechanical properties and geometry of the sphere and the surrounding gel. $\bar{E}$ is the average energy density of the incident field. The time average is over several cycles of the carrier frequency (microseconds) but typically varies over the period of the amplitude modulation (milliseconds). The acoustic radiation force on a steel sphere suspended in water was measured and found it agreed with the prediction of equation (1) within experimental error.

Generally, FIG. 1 illustrates a system 20 for measuring viscoelastic properties of a sample such as a gel. An acoustic radiation force source (source transducer) 22 is structured to generate acoustic radiation force at one or more frequencies. The acoustic radiation force is in the form of push pulses 24. A shear wave transmission device 26—in this particular embodiment, a sphere 28—is embedded in a mass 30. The mass 30 includes a gel 32, and, in other embodiments, may also include a biologic material such as tissue. The shear wave transmission device 26 is responsive to the acoustic radiation force source 22 and moves within the mass 30. A Doppler ultrasonic device (linear array transducer) 36 transmits a Doppler pulse sequence 38 in order to track the induced movement of the sphere 28 in the gel 32. Furthermore, the Doppler ultrasonic device 36 generates data representative of the induced motion of the sphere through the gel 32. As illustrated in FIG. 1, the angle θ is approximately 30° and represents the angle between the beam axes of the acoustic radiation force source 22 and the Doppler ultrasonic device 36.

Figure 1A:
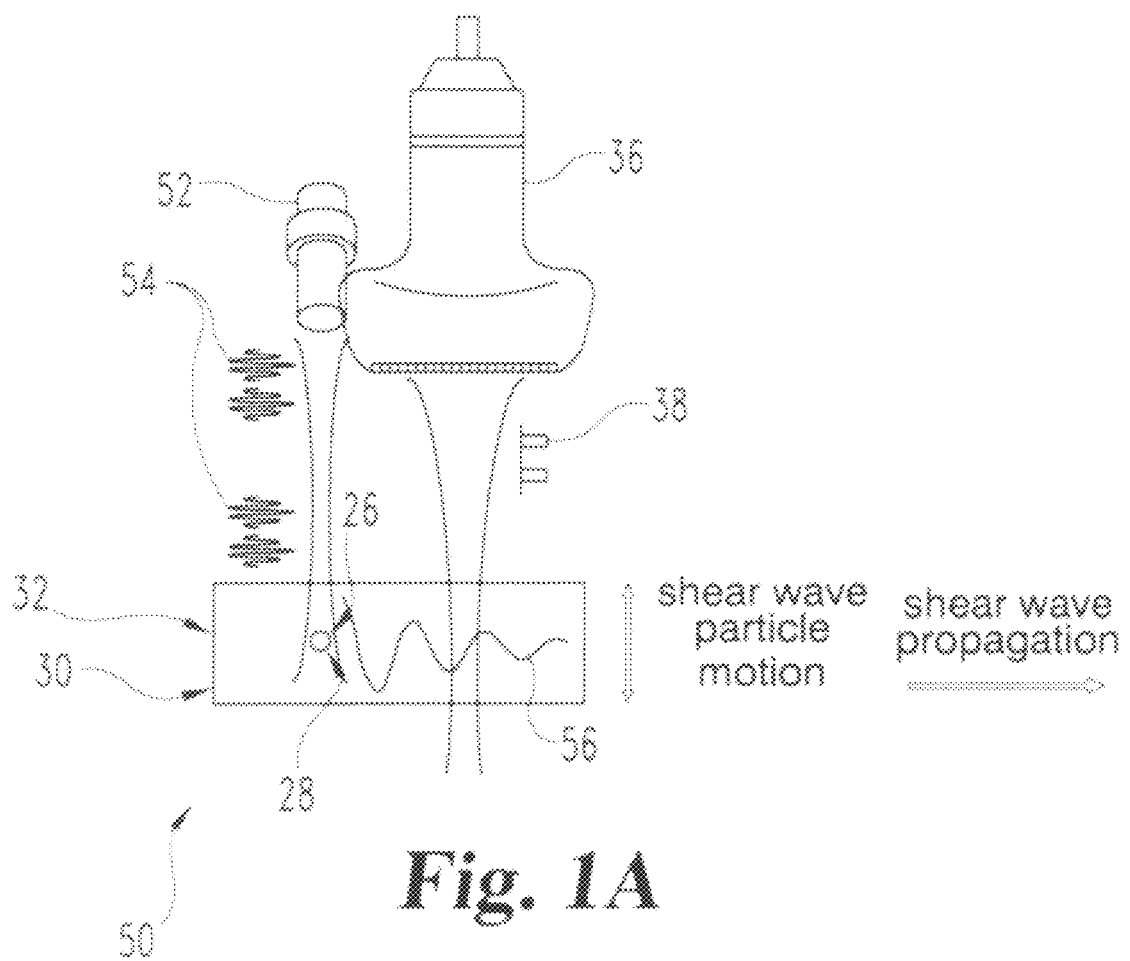
FIG. 1A is a diagrammatic view of a further system to measure viscoelastic properties that illustrates shear wave propagation in the sample in response to sinusoidal push pulses of acoustic radiation force.

In another non-limiting embodiment, FIG. 1A illustrates a system 50 for determining viscoelastic properties of a sample, such as a gel, by analyzing shear wave propagation through the gel. It should be noted that like reference numerals are used to identify like components in all the figures and their explanation is omitted. An acoustic radiation force source 52 generates sinusoidal push pulses 54. The sinusoidal push pulses 54 induce the sphere 28 to move in the mass 30 generating shear waves 56. The Doppler ultrasonic device 36 detects the shear waves 56 and generates data representative of the shear waves 56. This data can be processed to measure the viscoelastic properties of the mass 30 including a gel 32.

Referring back to FIG. 1, an experiment performed with a gel sample 32 containing a stainless steel sphere 28 is illustrated. Force is applied by the acoustic field of a circular, 19-mm-diameter, f/4, PZT element that is transmitting sine-wave bursts at the resonant frequency of 1 MHz. Bursts 200 ms in duration were transmitted every 2 s to induce a maximum sphere displacement >20 μm for gels containing 3% w/w gelatin. The pressure field from the source transducer 22 was measured in water using a recently calibrated PVDF membrane hydrophone (GEC-Research Ltd., Marconi Research Center, Chelmsford, UK.). The results were used to estimate a primary radiation force at 60 μN. The sphere 28 was positioned on the beam axis at the 76-mm radius of curvature of the source transducer 22. The location of the sphere 28 was tracked in time by measuring and integrating the instantaneous sphere velocity with the Doppler ultrasonic imaging device 36. A Siemens Sono-line Antares system was used to estimate sphere velocity via pulsed Doppler methods. A VF5-10 linear array transducer 36 was driven by 1 cycle, 7.27 MHz voltage pulses to transmit nominally 2.5 cycle 7 MHz acoustic pulses 38. Doppler pulse transmission was repeated for a fixed beam-axis position on the time interval $T_s$=76.8 μs. RF echo waveforms were sampled at 40 Msamples/s using the URI feature of the Antares system and stored for offline processing. The axes of the source transducer 22 and linear array transducer 36 intersected at the 1.5-mm-diameter steel sphere, and the beam axes were separated by θ=30° as illustrated in FIG. 1.

The demodulated complex envelope V[n, m'] was computed for each Doppler echo waveform. The sample index $1 \leq n \leq N$ counts echo samples within an echo waveform in what is commonly referred to as "fast time." The index $1 \leq m'M'$ counts the waveforms in "slow time." The lag-one correlation function estimate between adjacent pairs of echo waveforms is computed in accordance with equation (2) as follows:

$$\hat{\phi}[n,m] = V^*[n, 2m-1] B[n, 2m], \; m' = 2m-1. \tag{2}$$

The changed index from m' to m ($1 \leq m \leq M$) avoids counting by 2. The estimate of instantaneous sphere velocity $\hat{v}_s$ from complex correlation estimates is given by equation (3) as follows:

$$\hat{v}_s[m] = \left(\frac{-c}{4\pi f_c T_s \cos\theta}\right) \frac{1}{N_0} \sum_{n=n_0}^{n_0+N_0-1} \arg(\hat{\phi}[n, m]). \tag{3}$$

where: c is the compressional-wave speed of sound in the gel medium (1.5 mm/μs), $n_0$ marks the first fast-time sample in the region of interest near the sphere-echo peak, $N_0$ is the number of fast time samples in the region of interest, and arg(·) indicates the phase angle obtained from the arctangent of the ratio of imaginary to real parts of the argument. Sphere displacement is estimated by integrating velocity estimates, per the following relationship:

$$\hat{x}(t) \equiv \int_0^t \hat{v}_s(t') dt',$$

where t'=2 $mT_S$. Integration was performed numerically using a cumulative trapezoidal scheme.

Gelatin gel samples (250 bloom strength, Type B, Rousselot, Buenos Aires, Argentina) 32 were constructed to test acoustic radiation force measurements of shear modulus and viscosity. Gelatin powder and distilled water are heated in a water bath at a temperature between 65-68° C. for one hour and periodically stirred. When the sample is cooled to 50° C., 0.1% by weight formaldehyde is added and thoroughly mixed. Molten gelatin is poured into a cylindrical sample mold (diameter 7.5 cm, height 5.5 cm). Two or three stainless steel spheres 1.5 mm in diameter are widely dispersed within the cooling gel just prior to gelation. Samples with 3% or 4% w/w gelatin concentrations are homogenous except for the isolated spheres 28 that are separated by at least 1.5 cm.

Narrowband through-transmission measurements of compression-wave speed and attenuation coefficients were made on samples without steel spheres and with 4% gelatin concentration. Measurements made at 21° C. in degassed water were first calibrated using a castor oil sample. Two phantoms were measured every 0.5 MHz between 7 and 12 MHz. The slope of the attenuation coefficient as a function of frequency was estimated to be 0.027±0.003 dB mm$^{-1}$ MHz$^{-1}$. Using no alcohol in the sample, the average speed of compressional waves was c=1506±0.34 m s$^{-1}$ over the frequency range of the measurement.

The material properties of the gelatin gels 32 were verified independently through oscillatory rheometer experiments. Parallel plate shear experiments were conducted on an AR-G2 rheometer (TA Instruments, New Castle, USA). Circular specimens, 25 mm in diameter and 2-4 mm high, were molded from the same gelatin used to make the large samples containing spheres 28. After 1 day of gelation, the specimens were removed from the molds and attached to parallel plate fixtures using cyanoacrylate (Rawn America, Spooner, Wis., USA). Five percent strain was applied over a frequency range from 0.1 Hz to 10 Hz with 10 sample points per decade of frequency. For both concentrations of gelatin, the measured storage modulus was averaged over the test range giving 321±14 Pa and 640±17 Pa for 3% and 4% gelatin concentrations.

The rheological behavior of hydrogels at the molecular scale can be complex. Fortunately, gelatin gels typically behave as a continuum on a scale larger than the ultrasonic wavelength, so the displacement x(t) of an embedded sphere in gelatin may be described by a harmonic oscillator according to equation (4) as follows:

$$M_t \frac{d^2 x(t)}{dt^2} + R \frac{dx(t)}{dt} + kx(t) = F(t), \quad (4)$$

where F(t) is the driving force, $M_t$ is the total mass on which the force acts, R is the damping constant describing the resistance that the gel 32 imposes on sphere motion, and k is an elastic spring constant. Because the uniaxial load is applied along the source transducer 22 beam axis and movement of the sphere 28 is in the same direction, x and F are the axial components of the corresponding vectors. For a step change in force over time from a constant value to zero, F(t)=F$_0$(1−step(t)), the displacement obtained from equation (4) has the form given by equation (5) as follows:

$$x(t) = \begin{cases} x_0 & t \leq 0 \\ Ae^{-\alpha t}\cos(\omega_d t + \varphi) & t > 0. \end{cases} \quad (5)$$

where:
A is the displacement amplitude,
$\alpha = R/2M_t$ is a damping constant,
$\omega_d = \sqrt{\omega_0^2 - \alpha^2}$ is the resonant frequency with damping, and
$\omega_0 = \sqrt{k/M_t}$ is the resonant frequency without damping.
From the initial conditions, we find:

$$A = x_0/\cos\varphi \text{ and } \tan\varphi = -\alpha/\omega_d.$$

In estimating the total inertia of the system 20 when the embedded sphere 28 is in motion, the surrounding gel 32 is included. To the inertia of the sphere 28 itself, half of its volume is added at the density of the surrounding medium 30. Thus, the total mass that reacts to the radiation force is $M_t = M_s + M_a$, where $M_s$ is the mass of the sphere 28 and $$M_a = \frac{2}{3}\pi a^3 \rho_g$$

is the added mass of surrounding gel 32, where α is the sphere radius and $\rho_g$ is the density of the gel 32.

The spring constant k and damping constant R are related to the rheological properties shear modulus μ and shear viscosity η. It should be appreciated that the viscous drag force $F_d$ experienced by a 1.5-mm sphere as it moves through the incompressible, viscous gel at velocities <10 mm/s has a Reynolds number on the order of 0.02. Consequently, equation (4) gives the linear approximation $F_d(t) = Rv_s(t)$, and the classic Stokes equation for R is given by (6) as follows:

$$R = 6\pi a\eta, \quad (6)$$

where: the dynamic viscosity coefficient η has the SI units Pa s.

Applying an analysis parallel to Stokes' derivation shows that the elastic spring constant in the equation for the restoring force, $F_r(t) = -kx(t)$, is given by equation (7) as follows:

$$k = 6\pi a\mu, \quad (7)$$

where: μ is the shear modulus in Pa.

Combining equations (5)-(7), the measured time displacement can be modeled as a function of shear modulus and viscosity. The approach is to measure $M_t$ independently and then numerically fit normalized displacement estimates:

$$\hat{x}'(t) = \hat{x}(t)/\hat{x}_0$$

to model values:

$$x'(t) = x(t)/x_0$$

obtained from equations (5)-(7), with μ and η as free parameters. Normalization scales and shifts the response so that displacements have values between 0 and 1. Thus, μ and η can be estimated without knowledge of the applied force magnitude $F_0$.

Figure 2:
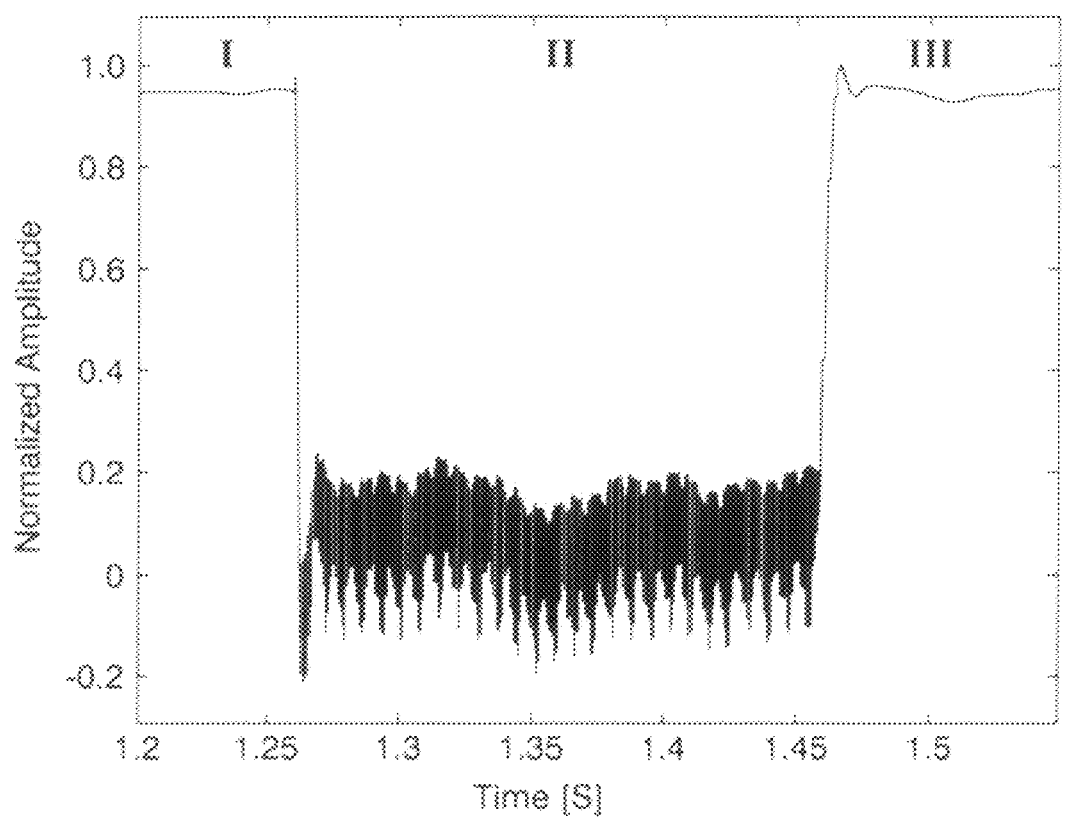
FIG. 2 provides a graph of sphere displacement versus slow time as determined from the change in Doppler echo phase.

These proposed model parameters were verified by conducting radiation force experiments. The 1 MHz source transducer transmitted 200 ms voltage bursts with the same amplitude in each experiment. Originally at rest, the sphere 28 was suddenly displaced away from the transducer 22 by the pulse a maximum distance $x_0$ (see FIG. 2) before being released to return to its original location. FIG. 2 provides a graph of sphere displacement versus slow time as determined from the change in Doppler echo phase. The sphere 28 is embedded in a 3% gelatin gel 32. Region I is a time period before radiation force is applied and the sphere 28 is at rest. Region II is a time period that the source transducer 22 is transmitting a 1 MHz CW burst and the sphere 28 is displaced away from the source transducer 22. Oscillations indicate cross talk between the source 22 and Doppler probes 36. Region III is the time period after the source transducer 22 is turned off and the sphere 28 returns to its original position. The imaging probe 36 measuring the sphere velocity was transmitting and receiving Doppler pulses during the entire process.

Figure 3:
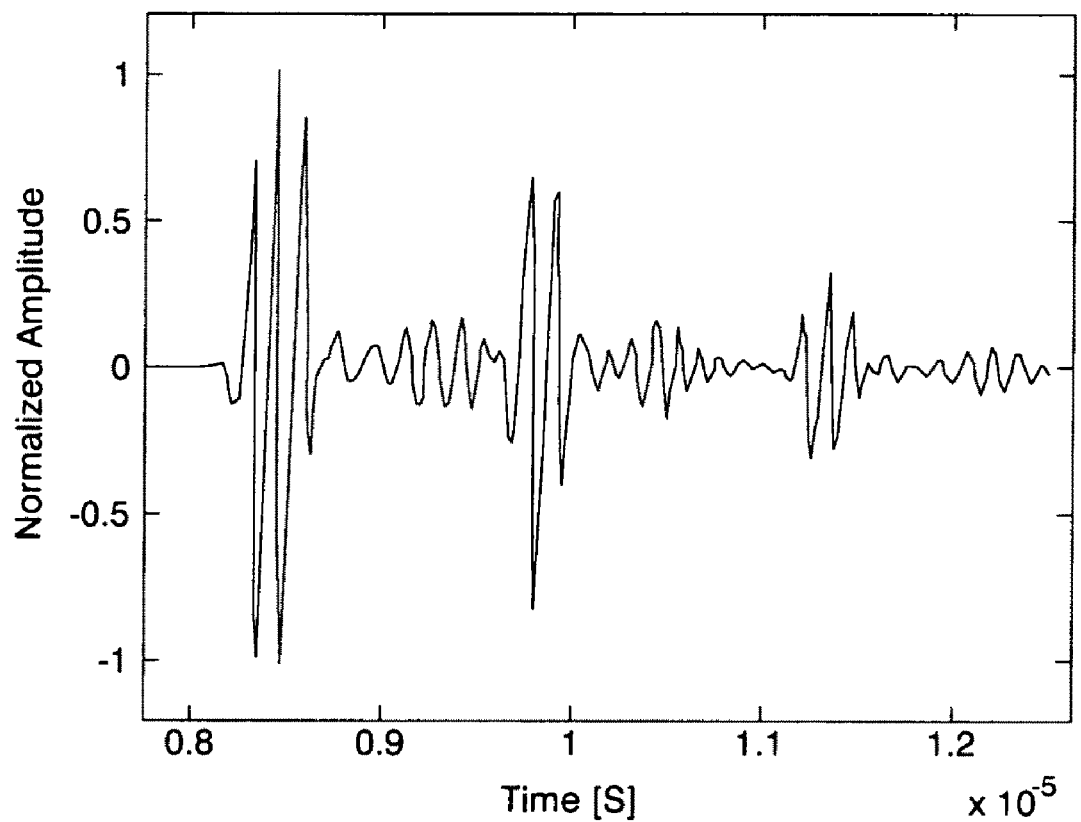
FIG. 3 provides a graph of a broadband Doppler echo waveform reflected by a sphere versus fast-time.

FIG. 3 provides an example of a broadband Doppler echo waveform versus fast-time. A single transmitted pulse is reflected from a steel sphere 28 in 3% gelatin gel 32. Multiple echoes indicate ringing of the sphere 28. Because the echo signal-to-noise ratio for tracking sphere velocity was very high, Doppler pulse durations were reduced from 4 to 2.5 cycles to temporally resolve the first echo from subsequent ringing echoes. Echo phase is estimated near the peak of the first echo in FIG. 3.

From the data of FIG. 2, the process for a specific experiment is illustrated. The spectral Doppler acquisition was initiated (Region I). After approximately 1.26 s, the source transducer 22 was turned on for 200 ms (Region II). The phase of the Doppler echo from the sphere 28 changed as the sphere 28 was displaced by the acoustic force. On the time axis of the figure at 1.46 s, the source transducer 22 is turned off (this time is set to t=0 in equation (5)) and the sphere 22 returns to the equilibrium position with the response of a slightly underdamped oscillator. The sphere displacement data was analyzed as the source pulse was turned off rather than turned on to avoid cross talk between the source 22 and Doppler probes 36 as seen in FIG. 2, region II. However either transition time could be made acceptable by filtering the echo waveform.

Figure 4:
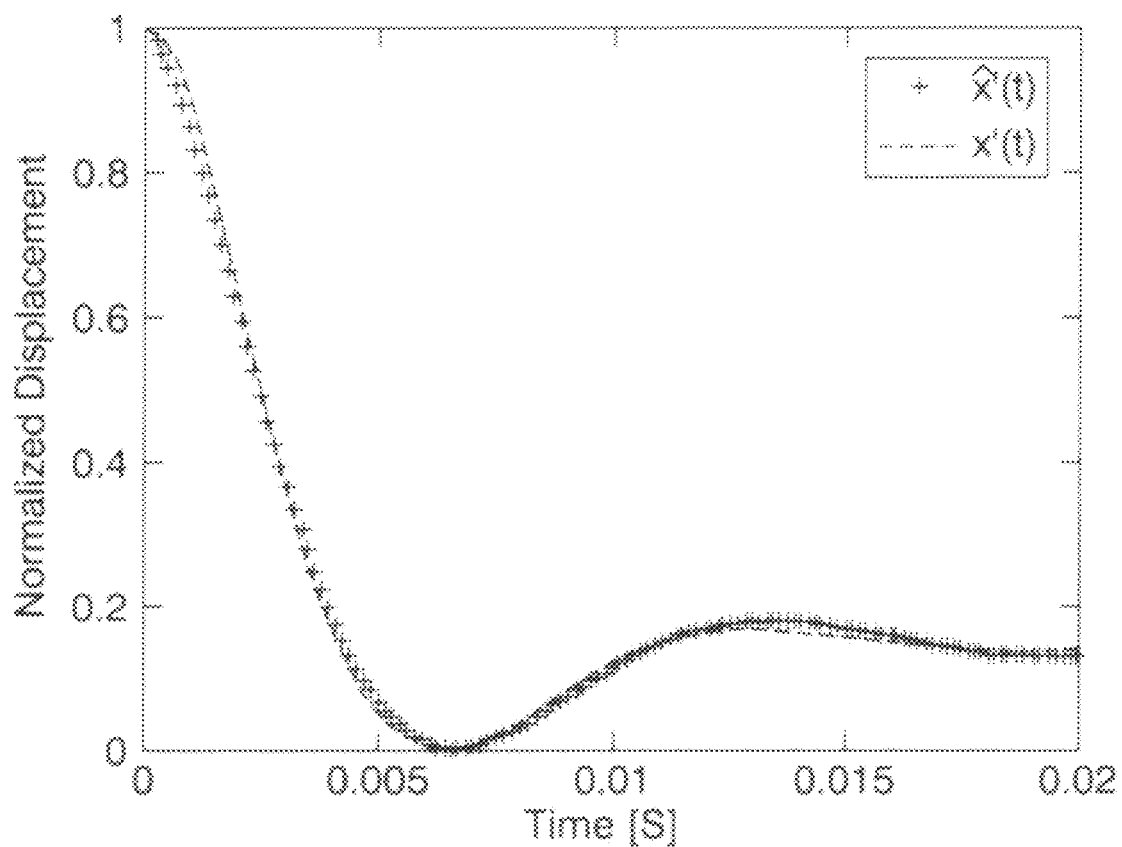
FIG. 4 is a graph comparing normalized sphere displacement measurements from region III in FIG. 2 with the model equation x'(t) from equation (5) as a function of slow time, 2 $mT_S$.

FIG. 4 is a graph comparing normalized sphere displacement measurements from Region III in FIG. 2 with the model equation x'(t) from equation (5) as a function of slow time, 2 $mT_s$. The minimum least-squares fit ($r^2$=0.996) was obtained for 3% gelatin gel aged one day to find µ=317, and Pa and η=0.57 Pa s. For an M-point displacement time series with normally distributed random error, the material parameters µ and η are chosen to give the smallest residual sum of squares in accord with equation (8) as follows:

$$r^2 = 1 - \frac{\sum_{m=1}^{M} (\hat{x}'[m] - x'[m])^2}{\sum_{m=1}^{M} (\hat{x}'[m] - \bar{x}')^2}, \tag{8}$$

$$\bar{x}' = \frac{1}{M} \sum_{m=1}^{M} \hat{x}'[m].$$

where: $r^2$ is bounded from above by 1 (perfect agreement between data and model) and from below by zero, although it can be negative.

For small displacements, there is close agreement between measurements and the model confirming that gel deformation is linear as required by equation (5). Furthermore, if the normalized displacement is time invariant, then we may express the model as a linear system according to the following equation (9):

$$x(t) = \int_{-\infty}^{\infty} dt' h(t - t')(1 - \text{step}(t'))$$

with impulse response $$h(t) = -\frac{dx}{dt} = Ae^{-\alpha t}(\alpha \cos(\omega_d t + \varphi) + \omega_d \sin(\omega_d t + \varphi)). \tag{9}$$

Equation (9) enables prediction of the displacement for any time-varying applied load for which the gel 32 responds linearly.

Figure 5:
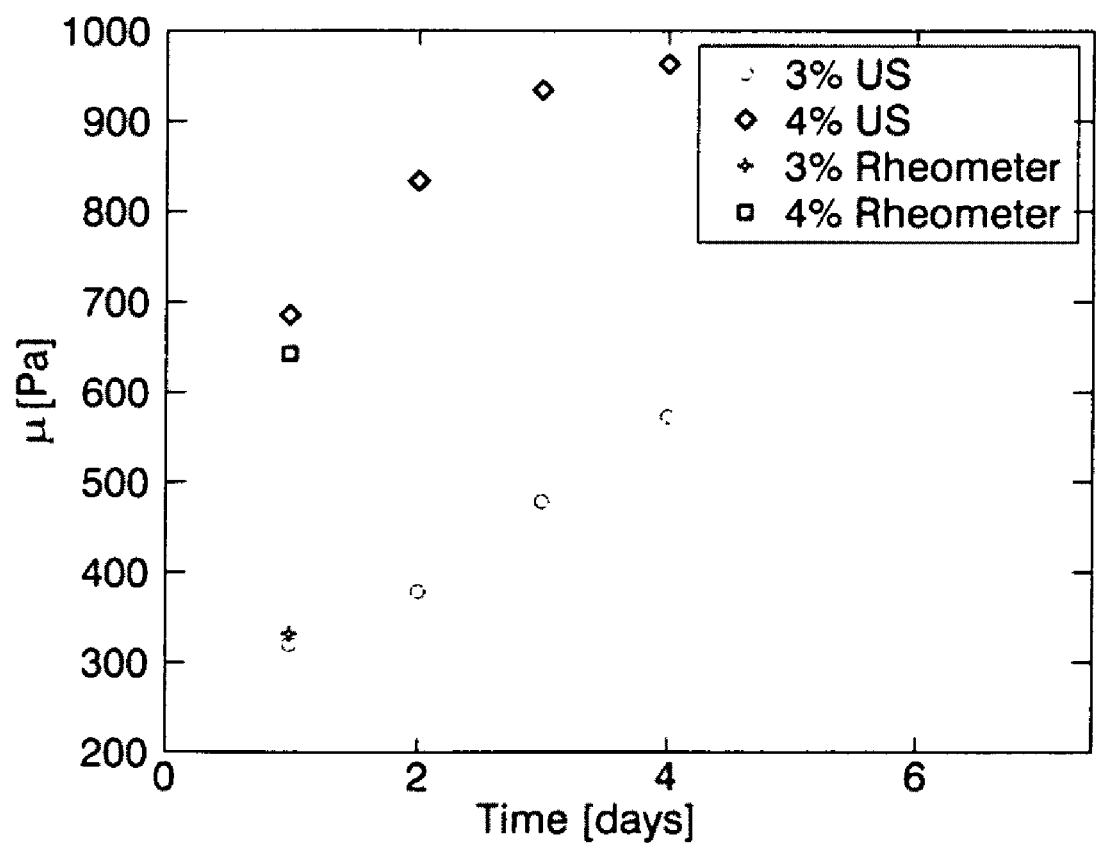
FIG. 5 is a graph plotting shear modulus as a function of gel age for 3% and 4% gelatin concentrations. Rheometer estimates of $\mu$ made on day 1 are also shown with error bars indicating ±1 sd.
Figure 6:
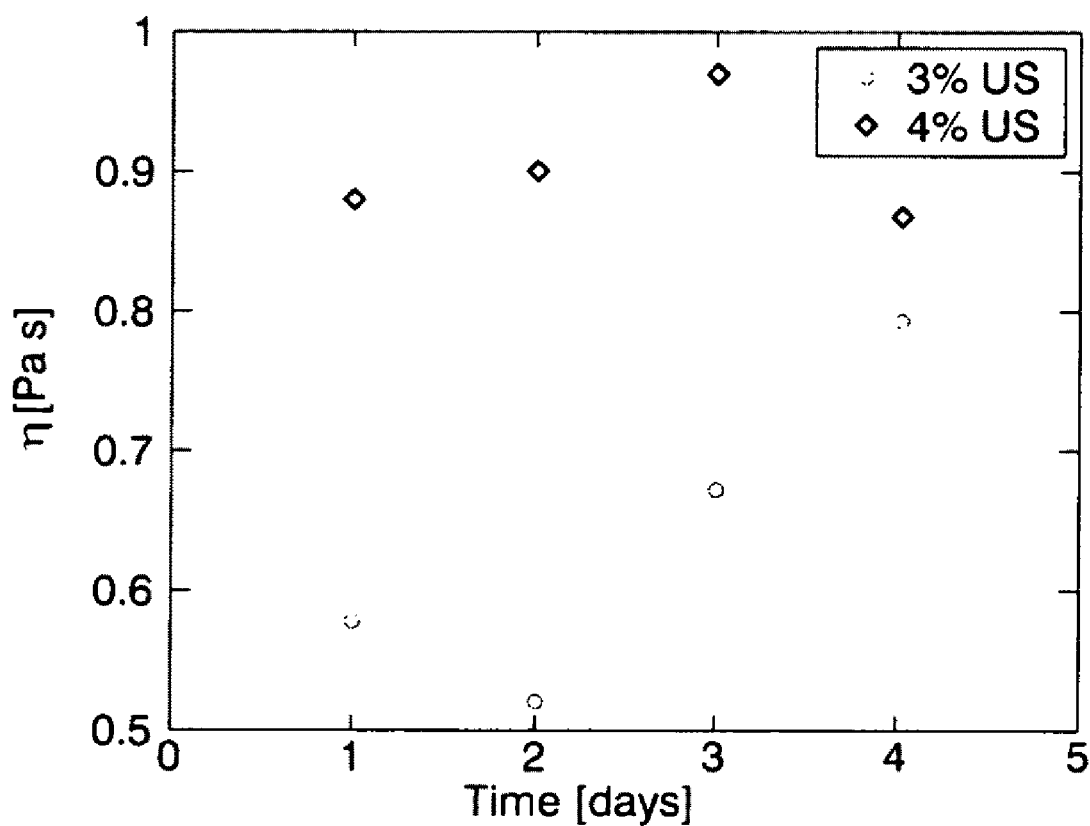
FIG. 6 is a graph plotting shear viscosity as a function of gel age for 3% and 4% gelatin concentrations.

Measurements of µ and η for 3% and 4% gelatin gels 32 conducted over four days are presented in FIG. 5 and FIG. 6, respectively. Without adding a strong chemical cross linker, gelatin gels 32 slowly increase their cross-link density, and thus gels 32 continue to stiffen over days. Although gelatin gel responses are not strictly time invariant, the change in the impulse response is negligible over the duration of any experiment. Estimated values of the modulus and viscosity for gels with C=4% gelatin concentration are larger than that at 3% for each day of the study. It has been found that the shear modulus varies with the square of gelatin concentration, $\mu \propto C^2$, between 1-5%. FIG. 5 suggests a concentration dependence of $C^{2.7}$ on day 1 and $C^{2.4}$ on day 3. Similarly, FIG. 6 shows that the shear viscosity coefficient increases linearly with gelatin concentration on day 1 and as $C^{1.3}$ on day 3.

As indicated in FIG. 5, rheometer measurements of the shear storage modulus were also made on day 1 for both gelatin concentrations. Five rheometer measurements were made on five different 3% gelatin samples to yield a mean and standard deviation of µr=321±14 Pa. The comparable radiation force estimate was 317 Pa. Three measurements were made on three different 4% samples to find pr 640±17 Pa. The comparable radiation force estimate is 681 Pa. Considering the rheometer measurements as a standard, radiation force estimates of shear modulus are accurate well within the observed day-to-day change in mean values.

Intrasample precision variability was estimated by measuring µ multiple times for a single sphere 28 in one gelatin sample 32. The percent standard deviation was found to be approximately 3.5% of the mean; for example, µ=317±11 Pa. Boundary variability, i.e., proximity of each steel sphere 28 to the gel sample surfaces, was examined by averaging µ measurements for different spheres 28 placed in one gelatin sample 32. That standard deviation was approximately 7% of the mean. Intersample variability for µ was larger, 20% of the mean, primarily because of differences in gel preparation. The relatively small random experimental error is a consequence of the high echo signal-to-noise ratio.

These empirical results suggest mechanical properties of gel 32 are primary factors determining the ultrasonic sampling rate for pulsed-Doppler velocity estimation. Discussion accompanying equations (5)-(7) explains that the time-varying displacement amplitude, the frequency, and the phase are functions of µ and η. Estimation accuracy and precision will vary with the sampling rate depending on the bandwidth of the displacement spectrum. For linear gels, the displacement spectrum is the spectrum of the applied force filtered by the mechanical system response of the gel, H(ω; µ,η); where H(ω; µ,η) is the temporal Fourier transform of equation (9) parameterized by the material properties.

The model spectrum of interest is the squared magnitude of the temporal Fourier transform of x'(t) from equation (5). It has the Lorentz form as follows:

$$|X'(\omega)|^2 + \frac{1}{\alpha^2 + (\omega - \omega_d)^2}.$$

The 3 dB, 6 dB, and 20 dB bandwidths of the displacement spectrum are, respectively:

$$\Delta \omega = R/M_r, \sqrt{3}/M_r, \text{ and } \sqrt{99}/M_r.$$

Therefore the upper limit on angular frequency is given by equation (10) as follows:

$$\omega_{max} = \omega_d + \Delta\omega/2 = \sqrt{\omega_0^2 - \alpha^2 B \alpha}, \tag{10}$$

where B=1, $\sqrt{3}$, or $\sqrt{99}$ for the 3 dB, 6 dB, or 20 dB bandwidths.

Figure 7:
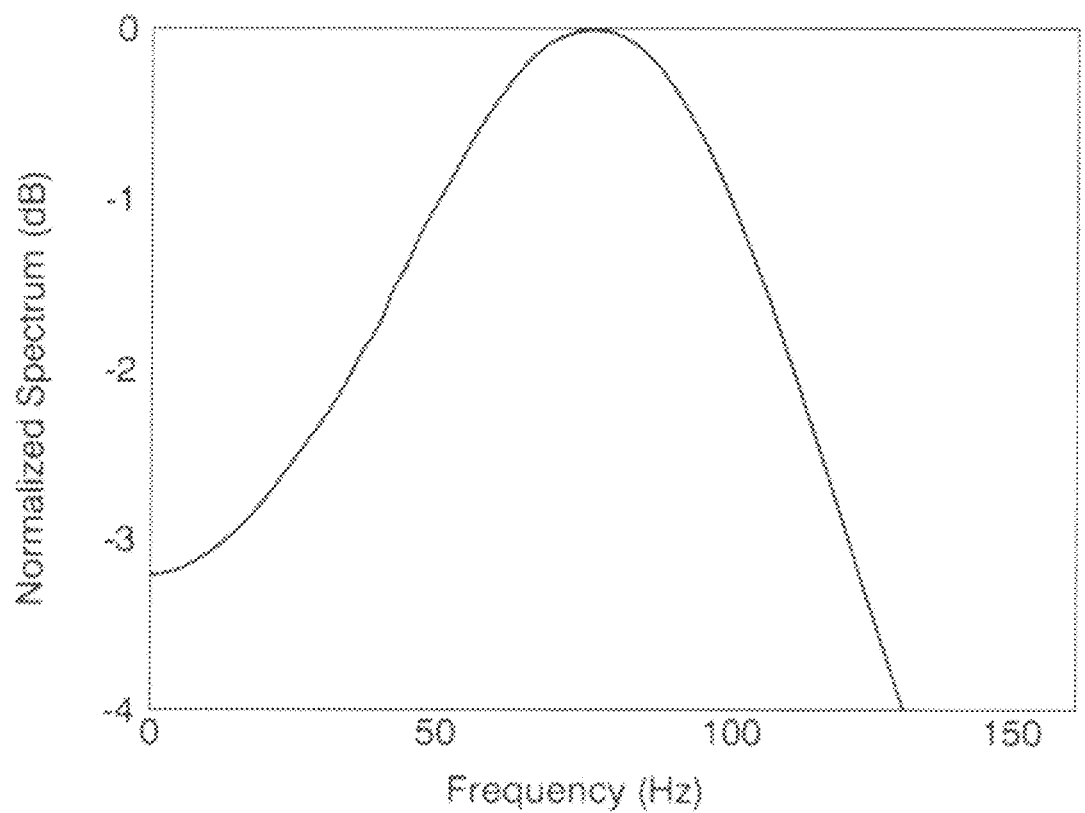
FIG. 7 provides a graph of the power spectrum of the displacement for the model parameters from 3% gel on day 1 with $\mu$=317 Pa and $\eta$=0.57 Pa s.

To illustrate, FIG. 7 displays the displacement spectrum corresponding to the parameters for gelatin measurements on day 1 for a 3% sample where µ=317 Pa and η=0.57 Pa s. The highest frequency in the 3 dB bandwidth is found from equation (10) to be $f_{max} = \omega_{max}/2\pi = 120$ Hz. The highest frequencies in the 6 dB and 20 dB bandwidths are 152 Hz and 510 Hz, respectively.

The sampling theorem for bandlimited signals states that the minimum sampling rate needed to avoid aliasing is twice the value of the maximum frequency in the bandwidth. However, we must further increase the rate by the number of pulses in the velocity estimator ensemble, $M_e$. That is, according to equation (11) as follows:

$$f_s \geq 2 M_e f_{max} = \frac{M_e}{\pi}\left(\sqrt{\omega_0^2 - \alpha^2} + B\alpha\right) = \frac{M_e}{\pi}\left(\sqrt{\frac{6\pi a \mu}{M_t} - \left(\frac{3\pi a \eta}{M_t}\right)^2} + \frac{3\pi B a \eta}{M_t}\right). \quad (11)$$

For the experiments described in the previous paragraph, with adoption of a 6 dB bandwidth limit and $M_e=2$, the pulse-repetition frequency (PRF=$f_s$) must exceed 608 Hz to avoid aliasing.

To decide on an acceptable lower bound on the sampling frequency, the Doppler measurements were oversampled at $f_s=13$ kHz, and then incrementally downsampled, being careful to apply the appropriate low-pass anti-aliasing filter as the Nyquist frequency changed, before processing. Estimates of $\mu$ and $\eta$ were correspondingly obtained as a function of $f_s$. A 15 dB bandwidth was sufficient to eliminate estimation errors within the intra-sample random error range of 7%.

Quick estimates of $\mu$ and $\eta$ may be made for a well-calibrated experimental system. If $M_t$ and $\alpha$ are known, then $\eta$ can be found directly from the 3 dB bandwidth of the step response, $\eta =$ $$M_t \Delta \omega_{3dB}/6\pi\alpha.$$

Applying this result and an estimate of the spectral peak to the expression for the resonant frequency $\omega_d$, $\mu$ can also be estimated.

A damped harmonic oscillator model accurately predicts the movement of a hard sphere embedded in a congealed hydrogel to a sudden change in acoustic radiation force. This result suggests that the gel responds linearly to the force. The shear modulus and shear viscosity were estimated with 7% intra-sample random experimental error by interpreting model parameters in terms of rheological elements. The radiation force estimates of shear modulus at two gel concentrations closely agree with independent measurements of the gels using a rheometer. These results can be extended to measure viscoelastic properties of 3-D cell cultures remotely to maintain sterile conditions.

Figure 8:
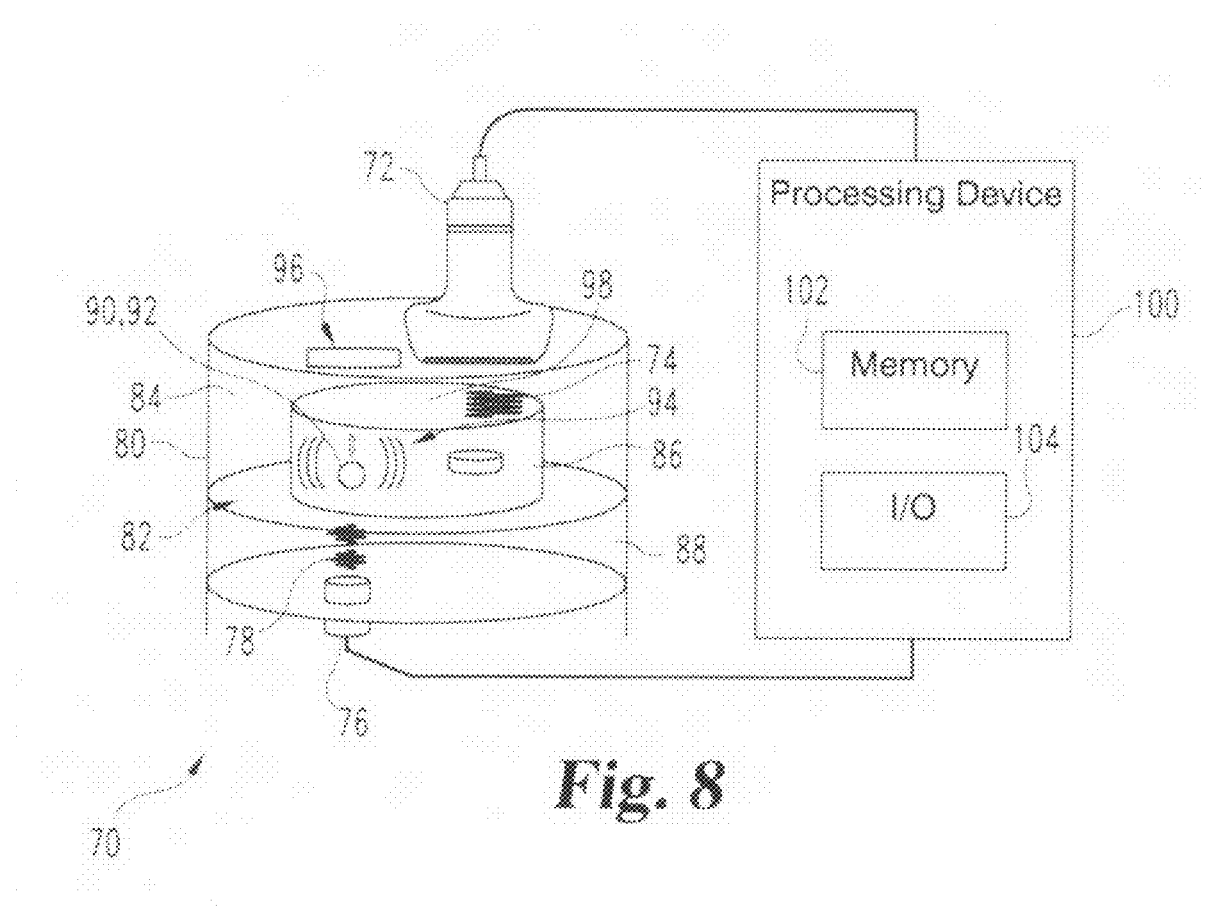
FIG. 8 is a diagrammatic view of a system for evaluating a biologic material with a shear wave transmission device in the form of an approximately spherical structure.

Certain embodiments of the present application are directed to an apparatus and method for estimating and imaging mechanical properties of cell cultures, engineered biological tissues, and the like. In one form, this apparatus includes one or more ultrasound emitting devices (transducers) that first apply an acoustic radiation force to vibrationally displace a sphere embedded in the medium and generate shear waves. This sphere is a form of a shear wave transmission device. One example of such an arrangement is the system 70 illustrated in FIG. 8. FIG. 8 illustrates a system 70 including a Doppler ultrasonic imaging device 72 in the form of a 1-D linear array that transmits a Doppler pulse sequence 74 and an acoustic radiation force source 76 that transmits push pulses 78. A sample mass 80 is positioned between the Doppler ultrasonic imaging device 72 and the radiation force source 76. Also included is a liquid 82 for cell culture 84 and a cell culture co-layer 86 therein including a gel 88 and a shear wave transmission device 90 in the form of a sphere 92, which generates shear waves 94 in response to the push pulses 78 from the acoustic radiation force source 76. A sound absorber 96 is also positioned on the outside of the mass 80 and further the cell culture co-layer 86 is stood off from the radiation force source 76 by a water bath 98.

The equipment used in this system 70 includes the Doppler ultrasonic imaging device 72 to detect mechanical response to acoustic radiation force from an appropriate source 76, and a processing device 100 to analyze corresponding data and provide output representative of one or more desired mechanical properties from the resulting shear waves 94. Processing device 100 executes operating logic that can define various models, conversions, controls, data management, and/or other regulation functions. This operating logic may be in the form of dedicated hardware, such as a hard-wired state machine, programming instructions, and/or a different form as would occur to those skilled in the art. The processing device 100 may be provided as a single component or a collection of operatively coupled components; and may be comprised of digital circuitry, analog circuitry, or a hybrid combination of both of these types. When of a multi-component form, it may have one or more components remotely located relative to the others. Also, it can include multiple processing units arranged to operate independently, in a pipeline processing arrangement, in a parallel processing arrangement, and/or such different arrangement as would occur to those skilled in the art. In one embodiment, the processing device 100 is a programmable microprocessing device of a solid-state, integrated circuit type that includes one or more processing units and memory. Device 100 can include one or more signal conditioners, modulators, demodulators, Arithmetic Logic Units (ALUs), Central Processing Units (CPUs), limiters, oscillators, control clocks, amplifiers, signal conditioners, filters, format converters, communication ports, clamps, delay devices, memory devices, and/or different circuitry or functional components as would occur to those skilled in the art to perform the desired communications.

Processing device 100, as illustrated, includes one or more types of memory 102, such as solid-state electronic memory, magnetic memory, optical memory, or a combination of these. This memory 102 could be removable, like an optical disk (such as a CD ROM or DVD); an electromagnetically encoded hard disk, floppy disk, tape, or cartridge media; or a different form as would occur to those skilled in the art. In one embodiment, at least a portion of the memory 102 is operable to store operating logic for the processing device 100 in the form of software programming instructions. Alternatively or additionally, memory 102 can be arranged to store data other than programming.

The processing device 100 also includes operator Input/Output (I/O) 104. Output devices could include a display of any type, such as a plasma, Cathode Ray Tube (CRT), or Liquid Crystal Display (LCD) type; and may further include one or more other operator output devices, such as a printer, an aural output system and/or different output device type as would occur to those skilled in the art. Input devices may include a conventional mouse and keyboard, a trackball, light pen, voice recognition subsystem, touch screen matrix, and/or different input device type as would occur to those skilled in the art.

Figure 9:
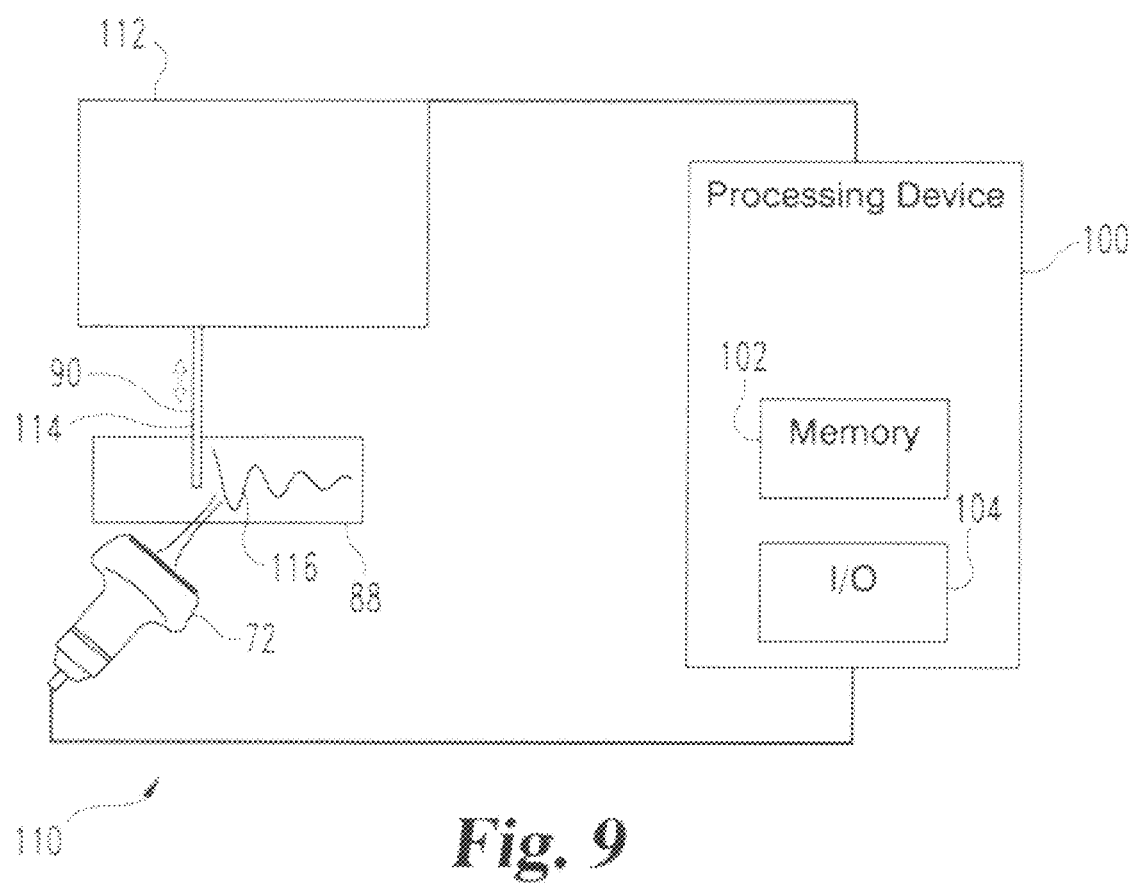
FIG. 9 is a diagrammatic view of another system for evaluating a biologic material with a shear wave transmission device in the form of a needle.

Alternatively or additionally, in a further embodiment of the application shown in FIG. 9, a system 110 includes an acoustic radiation force source 112 and a shear wave transmission device 90 that is responsive to an acoustic radiation force; where like reference numerals refer to like features previously described. In this embodiment, the shear wave transmission device 90 is in the form of a needle 114, such as a biopsy needle, that is inserted into the medium 88 and vibrated along its axis to generate shear waves 116. During and after vibration, ultrasound is again applied to image shear waves 116 in the medium 88 that propagate from the vibrating sphere or needle 114. By measuring the local wavelength of the shear waves 116, the shear modulus and viscous coefficient of the medium surrounding the vibrating element can be estimated.

Shear wave imaging with a vibrating sphere 92 (FIG. 8) and needle 114 (FIG. 9) have both been laboratory tested. In the case of the vibrating sphere 92, calibration included measuring the "impulse response function" of the device. That is, a constant acoustic radiation force is applied to an embedded sphere 92 with a source transducer 76 and then suddenly released. From measurements of the movement patterns of the sphere 92 after release, mechanical properties were estimated using the disclosed techniques and were compared with independent measurements. Subsequently, harmonic radiation forces were applied to embedded spheres 92 to: (a) observe the sensitivity of the measurement; and (b) compare with standard but independent measurements of mechanical properties.

In the case of the vibrating needle 114, time dependence and spatial dependence of shear waves emanating from the needle 114 were measured. The goal was to estimate sensitivity and frequency response. In still a further experiment, the needle 114 was used to produce surface waves (Rayleigh-Lamb waves, Love waves) with Optical Coherence Tomography (OCT). This experiment showed feasibility of using proposed techniques for calibrated estimation of surface material properties—potential applications include skin material properties evaluation (can be an indicator of aging, skin cancer, effect of ointments (medicaments) on skin properties, healing of skin, cosmetics etc.).

Figure 10:
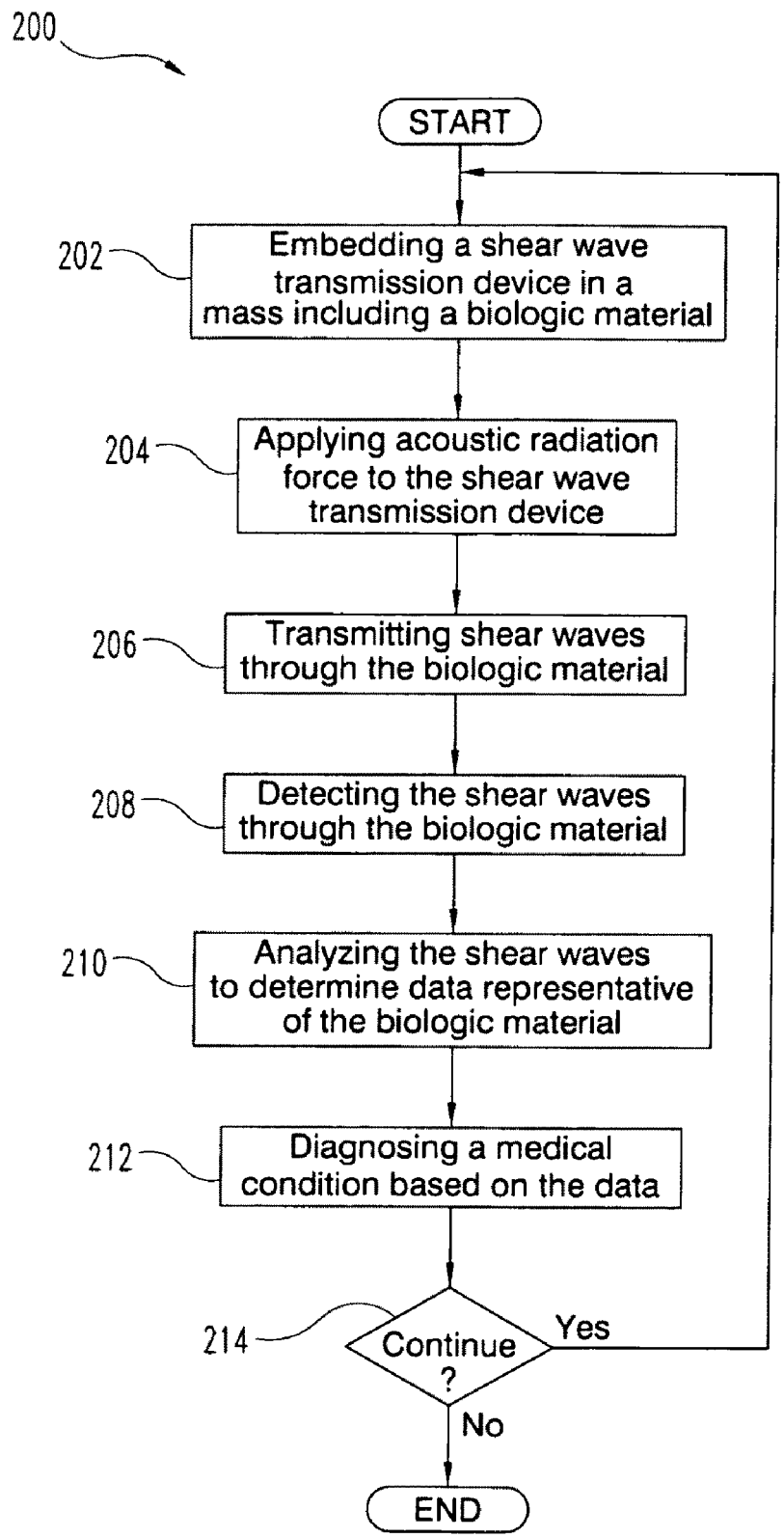
FIG. 10 is a flowchart depicting an operating procedure for evaluating a biologic material with a shear wave transmission device.

FIG. 10 is a flowchart 200 depicting an operating procedure 200 for evaluating a biologic material. In operation 202, a shear wave transmission device is embedded in a mass, such as a gel, including a biologic material, e.g., a cell culture and/or tissue. Such tissue may be removed from a human patient, animal, or other organism for evaluation or may be evaluated in vivo. The shear wave transmission device may include an approximately spherical structure or a needle, such as a biopsy needle, to name just a couple of examples. By way of nonlimiting examples, the equipment from one or more of systems 20, 50, 70, and/or 110 could be utilized to perform some or all of procedure 202. Next, in operation 204, an acoustic radiation force is applied to the shear wave transmission device. During operation 206, shear waves are transmitted from the shear wave transmission device through the biologic material. The shear waves are detected by a Doppler ultrasonic device in operation 208, which also generates data representative of the shear waves. In operation 210, the data is analyzed and processed for estimating and imaging mechanical properties of the biologic material, including cell cultures, biological tissues, and the like. These analyses are used in operation 212 for diagnosing a medical condition, e.g., discriminating between benign and malignant tumors, such as breast lesions, aging, skin cancer, effect of ointments (medicaments) on skin properties, healing of skin, and cosmetics. Finally, in operation 214, the operating procedure 200 may begin again or may terminate.

Many further embodiments of the present invention are envisioned. For example, in one form an apparatus to evaluate a biologic material includes an acoustic radiation force source structured to generate acoustic radiation force at one or more frequencies; a shear wave transmission device to embed in a mass including the biologic material that is responsive to the acoustic radiation force source to transmit shear waves through biologic material; a Doppler ultrasonic device to detect the shear waves and generate data representative thereof; and a processing device to determine one or more mechanical properties of the biologic material.

In still another embodiment, a method includes at least partially embedding a shear wave transmission device in a mass, including a biologic material; applying an acoustic radiation force to the shear wave transmission device at one or more frequencies; transmitting shear waves through the biologic material from the shear wave transmission device in response to the acoustic radiation force; and detecting the shear waves with the Doppler ultrasonic device to provide data representative of one or more mechanical properties of the biologic material.

Still another embodiment includes a system with a medium including a biologic material; a shear wave transmission device at least partially embedded in the medium that is responsive to acoustic radiation force to transmit shear waves through the biologic material; and equipment to detect the shear waves and generate data representative of one or more shear characteristics of the biologic material.

A further embodiment includes means for embedding a shear wave transmission device in a mass including a biologic material; means for applying acoustic radiation force to the shear wave transmission device at one or more frequencies; means for transmitting shear waves through the biologic material from the shear wave transmission device in response to the acoustic radiation force; and means for detecting shear waves with a device to provide data representative of one or more mechanical properties of the biologic material.

Still another embodiment includes an ultrasonic technique for estimating viscoelastic properties of biologic material is provided. An acoustic radiation force is applied to deform the material locally while Doppler pulses track the induced movement. In one form, an embedded scattering sphere is included and a single-element, spherically-focused, circular piston element transmits a continuous-wave burst to apply and remove a radiation force to the sphere. Simultaneously, a linear array and spectral Doppler technique are applied to track the position of the sphere over time. The shear modulus and shear viscosity are estimated by applying a harmonic oscillator model to measurements of time-varying sphere displacement. From this model, an impulse response function can be determined from which material properties for other load functions can be estimated. In another form, a needle is at least partially embedded in the biologic medium to impart acoustic radiation force in addition to or instead of a sphere.

Any experimental (including simulation) results are exemplary only and are not intended to restrict any inventive aspects of the present application. Any theory, mechanism of operation, proof, or finding stated herein is meant to further enhance understanding of the present invention and is not intended to make the present invention in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. While the invention has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any claims that follow are desired to be protected.

What is claimed is:

1. An apparatus, comprising:
    an acoustic radiation force source structured to generate acoustic radiation force at one or more frequencies;
    a shear wave transmission device to embed in a mass including a biologic material, the shear wave transmission device being responsive to the acoustic radiation force source to transmit shear waves through the biologic material;
    a doppler ultrasonic device to detect the shear waves and generate data representative thereof; and
    a processing device to determine one or more mechanical properties of the biologic material from the data.

2. The apparatus of claim 1, wherein the shear wave transmission device includes a needle.

3. The apparatus of claim 1, wherein the shear wave transmission device includes an approximately spherical structure inside the mass.

4. The apparatus of claim 1, wherein the processing device includes means for determining at least one of: (a) a wavelength of the shear waves in the biologic material, (b) shear modulus of the biologic material, and (c) viscous coefficient of the biologic material.

5. The apparatus of claim 1, further comprising means for providing the biologic material as a form of a cell culture and the mass including a gel.

6. The apparatus of claim 1, wherein the processing device is structured to evaluate a surface characteristic of a tissue included in the biologic material.

7. The apparatus of claim 1, further comprising a display to provide one or more images representative of the shear waves.

8. A method, comprising:
    at least partially embedding a shear wave transmission device in a mass including a biologic material;
    applying acoustic radiation force to the shear wave transmission device at one or more frequencies;
    transmitting shear waves through the biologic material from the shear wave transmission device in response to the acoustic radiation force; and
    detecting the shear waves with a doppler ultrasonic device to provide data representative of one or more mechanical properties of the biologic material.

9. The method of claim 8, which includes evaluating the data to discriminate between one or more cell types in the mass.

10. The method of claim 8, which includes diagnosing a medical condition based on the data.

11. The method of claim 8, which includes generating an image representative of the shear waves.

12. The method of claim 8, wherein the one or more mechanical properties include at least one of: (a) a wavelength of the shear waves in the biologic material, (b) shear modulus of the biologic material, and (c) viscous coefficient of the biologic material.

13. The method of claim 8, which includes evaluating a surface characteristic of a tissue, wherein the biologic material includes the tissue.

14. The method of claim 8, which includes preparing a bioengineered material based on the one or more mechanical properties.

15. The method of claim 8, wherein the shear wave transmission device includes a needle.

16. The method of claim 8, wherein the shear wave transmission device includes an approximately spherical structure inside the mass.

17. An apparatus, comprising:
    means for embedding a shear wave transmission device in a mass including a biologic material;
    means for applying acoustic radiation force to the shear wave transmission device at one or more frequencies;
    means for transmitting shear waves through the biologic material from the shear wave transmission device in response to the acoustic radiation force; and
    means for detecting shear waves.

18. The apparatus of claim 17, further comprising means for processing the shear waves to provide data representative of one or more mechanical properties of the biologic material.

19. The apparatus of claim 18, wherein the means for processing determines at least one of: (a) a wavelength of the shear waves in the biologic material, (b) a shear modulus of the biologic material, and (c) a viscous coefficient of the biologic material.

20. The apparatus of claim 18, wherein the means for processing is structured to evaluate a surface characteristic of a tissue included in the biologic material.

21. An apparatus, comprising:
    an acoustic radiation force source structured to generate acoustic radiation force at one or more frequencies;
    a transmission device to embed in a mass, wherein the acoustic radiation force source induces motion in the shear wave transmission device;
    a doppler ultrasonic device to detect the induced motion of the transmission device and generate data representative thereof; and
    a processing device to determine one or more mechanical properties of the mass from the data.

22. The apparatus of claim 21, wherein the transmission device is an approximately spherical structure inside the mass.

23. The apparatus of claim 21, wherein the mass includes a gel.

24. The apparatus of claim 21, wherein at least one of the mechanical properties of the mass includes a shear modulus of the mass or a viscous coefficient of the mass.

* * * * *